(12) United States Patent
Koehler et al.

(10) Patent No.: US 12,008,753 B2
(45) Date of Patent: Jun. 11, 2024

(54) SYSTEM FOR DETERMINING A TISSUE-SPECIFIC PROPERTY

(71) Applicant: KONINKLIJKE PHILIPS N.V., Eindhoven (NL)

(72) Inventors: Thomas Koehler, Norderstedt (DE); Sven Kabus, Hamburg (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 401 days.

(21) Appl. No.: 17/422,942

(22) PCT Filed: Jan. 16, 2020

(86) PCT No.: PCT/EP2020/051063
§ 371 (c)(1),
(2) Date: Jul. 14, 2021

(87) PCT Pub. No.: WO2020/148407
PCT Pub. Date: Jul. 23, 2020

(65) Prior Publication Data
US 2022/0122247 A1 Apr. 21, 2022

(30) Foreign Application Priority Data

Jan. 18, 2019 (EP) .................................. 19152536

(51) Int. Cl.
*G06T 7/00* (2017.01)
*A61B 5/085* (2006.01)
(Continued)

(52) U.S. Cl.
CPC ............ *G06T 7/0012* (2013.01); *A61B 5/085* (2013.01); *A61B 6/5217* (2013.01); *G06T 7/337* (2017.01);
(Continued)

(58) Field of Classification Search
CPC ....... A61B 5/085; A61B 6/032; A61B 6/5217; G06T 2207/10081; G06T 2207/10088;
(Continued)

(56) References Cited

U.S. PATENT DOCUMENTS 8,965,071 B2 * 2/2015 Fox .................... G06V 10/50
382/128
9,076,201 B1 * 7/2015 Negahdar ............... G06T 7/38
(Continued)

FOREIGN PATENT DOCUMENTS

EP 2829233 A1 * 1/2015 ............. A61B 5/055
EP 2829233 A1 1/2015

OTHER PUBLICATIONS

Sandeep Bodduluri, "Computed Tomography Image Matching in Chronic Obstructive Pulmonary Disease," Jul. 23, 2018, Crit Rev Biomed Eng., available in PMC 2018, pp. 1-11.*
(Continued)

*Primary Examiner* — Omar S Ismail
(74) *Attorney, Agent, or Firm* — Larry Liberchuk

(57) ABSTRACT

The present invention refers to providing a system that allows to very accurately determine the state of a disease, like COPD, in a patient. The system (100) comprises a unit (101) for providing images of the region of interest corresponding to different states of the region of interest, a unit (102) for elastically registering the images to each other resulting in an elastic registration output, a unit (103) for determining a specific tissue region in an image, a unit (104) for determining a specific elastic registration output for the specific tissue region based on the determined elastic registration output, and a unit (105) for determining an elastic indicator for the specific tissue type based on the specific elastic registration output. Thus, a state of a disease that
(Continued)

influences the elastic properties of the specific tissue type can be determined very accurately.

13 Claims, 2 Drawing Sheets

(51) Int. Cl.
*A61B 6/00* (2006.01)
*G06T 7/33* (2017.01)
*G06T 7/38* (2017.01)

(52) U.S. Cl.
CPC ...... *G06T 7/38* (2017.01); *G06T 2207/30061* (2013.01)

(58) Field of Classification Search
CPC ......... G06T 2207/30061; G06T 7/0012; G06T 7/0016; G06T 7/33; G06T 7/337; G06T 7/38
See application file for complete search history.

(56) References Cited

U.S. PATENT DOCUMENTS

| | | | | |
|---|---|---|---|---|
| 9,406,146 | B2 * | 8/2016 | Wiemker | G06T 7/20 |
| 2007/0167784 | A1 * | 7/2007 | Shekhar | A61B 6/032 600/443 |
| 2010/0220901 | A1 * | 9/2010 | Matsumura | G01S 7/52074 382/128 |
| 2013/0279785 | A1 * | 10/2013 | Proksa | G06T 11/006 382/131 |
| 2014/0198964 | A1 * | 7/2014 | Von Berg | A61B 6/545 382/131 |
| 2014/0288420 | A1 * | 9/2014 | Goossen | A61B 6/482 600/427 |
| 2015/0161786 | A1 * | 6/2015 | Seifert | A61B 6/5211 382/119 |
| 2015/0317792 | A1 * | 11/2015 | Wiemker | G06T 11/60 382/131 |
| 2016/0213303 | A1 * | 7/2016 | Hyde | G01S 13/88 |
| 2016/0213315 | A1 * | 7/2016 | Hyde | A61B 90/90 |
| 2017/0071571 | A1 * | 3/2017 | Lee | A61B 8/085 |
| 2018/0070905 | A1 * | 3/2018 | El-Baz | G06T 7/149 |
| 2019/0096064 | A1 * | 3/2019 | Yang | G06T 11/60 |

OTHER PUBLICATIONS

Keisaku Fujimoto, "Clinical analysis of chronic obstructive pulmonary disease phenotypes classified using high-resolution computed tomography," Oct. 16, 2006, Respirology (2006) 11,Asian Pacific Society of Respirology, pp. 731-737.*

Miranda Kirby, "A Novel Method of Estimating Small Airway Disease Using Inspiratory-to-Expiratory Computed Tomography," Aug. 23, 2017, Respiration 2017;94:, pp. 336-340.*

Eric A. Hoffman, "A Structural and Functional Assessment of the Lung via Multidetector-Row Computed Tomography," May 30, 2006, Proceedings of the American Thoracic Society vol. 3,2006, pp. 520-527.*

Peter K. Jeffery, "Comparison of the Structuraland Inflammatory Features of COPD and Asthma," Dec. 28, 2015, Chest, vol. 117,Issue 5,May 2000,Supplement 1pp. 251S-257S.*

N Sverzellati, "New insights on COPD imaging via CT and MRI," Oct. 20, 2022, International Journal of Chronic Obstructive Pulmonary Disease, International Journal of COPD 2007:2(3),pp. 301-309.*

Sandeep Bodduluri, "Recent Advances in Computed Tomography Imaging in Chronic Obstructive Pulmonary Disease," Jul. 24, 2017,Annals of the American Thoracic Society,vol. 15, Issue 3,pp. 281-286.*

PCT International Search Report, International application No. PCT/EP2020/051063, dated Mar. 18, 2020.

Fujimoto K. et al., "Clinical Analysis of Chronic Obstructive Pulmonary Disease Phenotypes Classified Using High-Resolution Computed Tomography", Respirology (2006) 11, 731-740.

Bodduluri S. et al., "Computed Tomography Image Matching in Chronic Obstructive Pulmonary Disease", Crit Rev Biomed Eng. 2016 ; 44(6): 411-425.

Kirby M. et al., "A Novel Method of Estimating Small Airway Disease Using Inspiratory-to-Expiratory Computed Tomography", Respiration 2017;94:336-345.

Bodduluri S. et al., "Registration Based Lung Mechanical Analysis of Chronic Obstructive Pulmonary Disease (COPD) Using A Supervised Machine Learning Framework", Academic Radiology. vol 20, issue 5, pp. 527-536, 2013.

Murphy K. et al., "Obstructive Pulmonary Function: Patient Classification Using 3D Registration of Inspiration and Expiration CT Images", The Second International Workshop on Pulmonary Image Analysis, 37-47 (2009).

Maintz J.B.A. et al., "A Survey of Medical Image Registration" Medical Image Analysis, vol. 2, pp. 1-36, (1998).

Sotiras A. et al., "Deformable Medical Image Registration: A Survey" IEEE Transactions on Medical Imaging, vol. 32, No. 7, pp. 1153-1190, Jul. 2013.

* cited by examiner

SYSTEM FOR DETERMINING A TISSUE-SPECIFIC PROPERTY

FIELD OF THE INVENTION

The invention relates to a system, a method and a computer program for determining a tissue-specific property in a region of interest of a patient.

BACKGROUND OF THE INVENTION

Many diseases, especially chronic diseases like chronic obstructive pulmonary disease (COPD), result in changes of the properties of tissue in an organ. For finding these property changes and thus for diagnosing the disease often functional tests of the organ are used together with medical images like CT or MR images. But, especially in the early stages of such diseases it is often difficult to accurately diagnose the disease, for instance, a certain special state of the disease, based only on the functional tests and the medical images, since in these early stages often the function of the organ is not yet disturbed and the change in the properties of the tissue does not reflect very well in the medical images.

SUMMARY OF THE INVENTION

It is an object of the present invention to provide a system, a method and a computer program that allow to very accurately determine the state of a disease like COPD in a patient.

In a first aspect of the present invention a system for determining a tissue-specific property in a region of interest of a patient is presented, wherein the region of interest comprises different tissue types, wherein the system comprises a) an image providing unit for providing at least two images of the region of interest, wherein the provided images correspond to different states of the region of interest, b) a registration unit for elastically registering the at least two provided images to each other based on image characteristics of the at least two provided images, wherein the registration results in determining at least one elastic registration output allowing to align the at least two provided images with each other, c) a specific tissue determination unit for determining a specific tissue region in the region of interest in at least one of the provided images, wherein the specific tissue region comprises all parts of the respective provided image corresponding to a specific tissue type, d) a specific elastic registration output determination unit for determining a specific elastic registration output for the specific tissue region based on the at least one determined elastic registration output, and e) a property determination unit for determining an elastic indicator for the specific tissue type based on the specific elastic registration output of the specific tissue region, wherein the elastic indicator is indicative of an elastic property of the specific tissue type.

Since the specific tissue determination unit determines a specific tissue region in at least one of the provided images in the region of interest, and since the specific elastic registration output determination unit determines a specific elastic registration output for the specific tissue region based on each determined elastic registration output, and since the property determination unit determines an elastic indicator for the specific tissue type based on the specific elastic registration output of the specific tissue region, wherein the elastic indicator is indicative of an elastic property of the specific tissue type, an indicator for an elastic property of a specific tissue, for instance, a tissue affected by a chronic disease, in a region of interest can be determined very accurately without any influence of other tissue types in the region of interest. Thus, also a state of a disease that influences the elastic properties of the specific tissue type can be determined very accurately.

The region of interest of a patient can refer to any region of the patient, for instance, to a specific organ of the patient, to a region surrounding an organ of the patient or to a region comprising a plurality of organs. Preferably, the region of interest comprises an organ of a patient that is affected by a disease. The organ can be a heart or a liver of the patient. Preferably, the organ is a lung of the patient. The different tissue types can refer to the tissue types that can be distinguished in the respective region of interest, for instance, functional tissue, connective tissue, muscle tissue, epithelial tissue, or more specific tissue types, like heart muscle tissue, vessel tissue, or preferably parenchyma tissue or bronchial tissue.

The image providing unit is adapted to provide at least two images of the region of interest. The image providing unit can be, for instance, directly connected to a medical imaging system used for acquiring the at least two images of the region of interest and directly provide the image data acquired by the medical imaging system. Moreover, the image providing unit can also be a part of the medical imaging system used for acquiring the at least two images. Alternatively, the image providing unit can be separate from a medical imaging system and/or can be connected, for instance, to a storage unit storing the at least two images of the patient. Further, the image providing unit can itself be configured as a storage unit storing the at least two images of the patient. Moreover, the image providing unit can be a selection unit that is adapted to select the at least two images that are provided by the providing unit from a plurality of images of the region of interest. For instance, a medical imaging system can provide a plurality of images of a region of interest, for instance, can provide a 4D image of a region of interest comprising images for different times, wherein the image providing unit, being a selection unit, can be adapted to select, for instance, two images from the plurality of images and provide the two images as the at least two images, or can be adapted to select all images of the 4D image and provide all images as the at least two images.

The at least two images can be acquired by using a medical imaging system, being, for instance, an MR system, an ultrasound system, a PET system, etc. Preferably, the medical imaging system is a CT system or an MR system. Moreover, the provided at least two images can be acquired using the same medical imaging system or can be acquired using different medical imaging system. Preferably, the provided at least two images are acquired using the same CT system. The provided at least two images can be 2D images or 3D images of the region of interest comprising pixels or voxels, respectively. In the following the term "voxel" is generally used to indicate an image element, wherein depending on if the respective image is a 3D image or a 2D image the term can also refer to "pixel".

The at least two images are acquired during different states of the region of interest. The different states can refer, for instance, to different phases of a heart during a cardiac cycle, different filling states, for instance, of a stomach, different positional states, based on a position of the patient, etc. Preferably, the different states refer to different states of a lung during a breathing cycle. Moreover, preferably the different states include at least one state of the lung at the end of inhalation and one state of the lung at the end of exhalation.

The registration unit is adapted to elastically register the at least two provided images based on image characteristics of the provided images. The image characteristics can refer, to structural characteristics, for instance, to anatomical features of the region of interest like the anatomical shapes and structures of an organ within the region of interest. Moreover, the image characteristics can refer to differences in the image values, for instance, to differences in the intensity values, of the provided images that can be observed. The provided images can then be registered such that corresponding image characteristics are identified in the provided images. Based on this identification of corresponding image characteristics in the provided images, the registration unit can be adapted to determine, for each provided image, a registration between the provided images resulting in the determination of at least one elastic registration output.

The elastic registration output is indicative of the displacement of the structural characteristics that is necessary for mapping the image characteristics of one provided image, for instance, a first image, to the corresponding image characteristics in another provided image, for instance, a second image. Preferably, the registration unit is adapted to register two provided images by determining an elastic registration output comprising for each voxel or pixel of the respective provided image, elastic registration information indicative on how the voxel or pixel has to be transformed to match a corresponding voxel or pixel of the other respective provided image. Alternatively, the registration unit can also be adapted to register the provided images by determining an elastic registration output comprising, for each voxel or pixel of a predefined region of interest, for instance, a predefined organ within the provided images elastic registration information.

Moreover, the registration unit is adapted to elastically register the at least two provided images to each other. If more than two images are provided, the registration unit can be adapted to select one of the provided images and to register all other images to the selected image. Furthermore, the registration unit can be adapted to register the provided images to each other, for instance, by registering subsequent images, respectively, when the images are sorted in correspondence with their place in a time-dependent process, like a cardiac cycle. For example, if the different states refer to different states of the lung during a breathing cycle, the registration unit can be adapted to sort the provided images into different distinguishable phases during the breathing cycle and to register at least one image of each distinguishable phase with at least one image of each of the other distinguishable phases. Preferably, the registration unit can be adapted to determine an elastic registration output for each registration, i.e. for each image. Alternatively, the registration unit can be adapted to select an output of a registration between two images as the elastic registration output, for instance, based on a quality criterion. Moreover, the registration unit can be adapted to determine an elastic registration output based on the output of all registrations, for instance, by averaging the output of all registrations.

The specific tissue determination unit is adapted to determine a specific tissue region in at least one of the provided images in the region of interest. The specific tissue determination unit can be adapted to determine the specific tissue region before or after the registration unit registers the provided images. Moreover, the registration unit can be adapted to further base the registration of two provided images on the determined specific tissue region, if the specific tissue determination unit is adapted to determine the specific tissue region before the registration. Preferably, the specific tissue determination unit is adapted to determine the specific tissue region in only one of the provided images, wherein since the provided images are registered to each other, the specific tissue region is also known in all other provided images. For instance, if the registration unit is adapted to select one provided image to which all other provided images are registered, the specific tissue determination unit can be adapted to determine the specific tissue only in the one selected image. Alternatively, the specific tissue determination unit is adapted to determine the specific tissue region in all of the provided images such that the determination of the specific elastic registration output can be based on the specific tissue region identified in all of the provided images. This allows to determine the specific elastic registration output with higher accuracy.

The specific tissue region is defined as comprising all parts of the respective image, i.e. all voxels or pixels of the respective image, corresponding to the specific tissue type that can be distinguished in at least one of the provided images, for instance, bronchial tissue. The specific tissue determination unit can be adapted to determine the specific tissue region automatically, for instance, based on predefined image characteristics of the specific tissue type, like specific gray values, a specific known structure or shape or a known location of the tissue type in the region of interest. An automatic determination can also be based, for instance, on machine learning algorithms that are trained to identify a specific tissue type in a region of interest. Alternatively, a specific tissue determination unit can be adapted to determine the specific tissue region in cooperation with a user, for instance, a physician. The specific tissue determination unit can in this case be adapted to present a provided image to a user and to prompt the user to delineate the parts of the image comprising the specific tissue type in the presented image, wherein the specific tissue determination unit then determines the specific tissue region based on the delineation of the user.

The specific elastic registration output determination unit is adapted to determine a specific elastic registration output for the specific tissue region based on the at least one determined elastic registration output. Preferably, if more than one elastic registration output is determined, the specific elastic registration output determination unit can be adapted to determine at least one specific elastic registration output for each determined elastic registration output. Alternatively, the specific elastic registration output determination unit can be adapted to determine only one specific elastic registration output based on the determined elastic registration outputs, for instance, by averaging the determined elastic registration outputs. Preferably, the specific elastic registration output determination unit is adapted to determine a specific elastic registration output of the specific tissue region by identifying, from the at least one elastic registration output, elastic registration information corresponding to the specific tissue region. For instance, the specific elastic registration output determination unit can be adapted to determine elastic registration information included in the elastic registration output belonging to a specific tissue region as specific elastic registration output. Preferably, the specific elastic registration output determination unit is adapted to identify elastic registration information in the at least one elastic registration output that belongs to pixels or voxels that are determined in an image belonging to the specific tissue region. For instance, the specific elastic registration output determination unit can be adapted to use the specific tissue region determined in the at least one image to determine voxels or pixels of the at least one image or another of the provided images belonging to the specific tissue region. In such an embodiment, the specific elastic registration output determination unit can be adapted, for instance, to use the registration information between two images to determine the pixels or voxels belonging to the specific tissue region in an image registered to the at least one image in which the specific tissue region was determined.

The property determination unit is adapted to determine an elastic indicator for the specific tissue type based on the specific elastic registration output of the specific tissue region. In particular, the property determination unit is adapted to determine the elastic indicator for the specific tissue type only based on the specific elastic registration output of the specific tissue region. Accordingly, parts of the registration output that do not refer to the specific tissue region and thus do not belong to the specific tissue type are not taken into account for determining the elastic indicator for the specific tissue type. For instance, elastic registration information from voxels outside of the specific tissue region is not taken into account during the determination of the elastic indicator. Moreover, for determining the elastic indicator of the specific tissue type the specific elastic registration output referring to all of the specific tissue, i.e. to the specific tissue region, is taken into account. Thus, the overall elastic indicator of the specific tissue type can provide a very accurate indication of the elastic properties of the specific tissue type.

If the specific elastic registration output determination unit provides more than one specific elastic registration output, the property determination unit can be adapted to determine the elastic indicator based on the provided more than one specific elastic registration output. Preferably, in such an embodiment the property determination unit is adapted to determine an elastic indication for each of the provided specific elastic registration outputs, wherein each of the determined elastic indicators is indicative for an elastic property of the specific tissue region. Moreover, the property determination unit can be adapted to determine only one elastic indicator from the more than one determined specific elastic registration outputs, for instance, by averaging.

The property determination unit can, for instance, be adapted to determine the elastic indicator based on known functional relations between the specific elastic registration output and/or the elastic registration information included in the specific elastic registration output and an elastic property of tissue. Moreover, the property determination unit can be adapted to determine the elastic indicator of a specific tissue type in comparison to an elastic indicator of the specific tissue type of a healthy subject. Alternatively, the property determination unit can also be adapted to determine as elastic indicator an absolute elastic indicator, for instance, an absolute elastic value of the specific tissue type.

In an embodiment, the system further comprises a health state determination unit for determining a health state of the patient based on the determined elastic indicator of the specific tissue type in the region of interest. Preferably, if more than one elastic indicator is determined by the property determination unit, the health state determination unit is adapted to determine the health state based on the determined elastic indicators. The health state determination unit can, for instance, be adapted to determine the health state of the patient based on a comparison of the determined elastic indicator with the elastic indicator of the specific tissue type of a healthy subject. Moreover, the health state determination unit can be provided with a list comprising elastic indicators of a specific tissue type and their relation to known diseases or disease states. The health state determination unit can then be adapted to determine as health state of the patient a specific disease or disease state from which the patient might suffer based on the list. Further, the health state determination unit can also be adapted to determine the health state based on a plurality of elastic indicators of a tissue type or of different tissue types. After the determination of the health state the health state determination unit can be adapted to present that determined disease or disease state to a user, for instance, together with a probability that the patient suffers from the respective disease. Preferably, the health state determination unit is adapted to determine as health state of a patient whether the patient is suffering from emphysema or obstructive bronchiolitis as phenotypes of COPD.

In an embodiment, the registration unit is adapted to determine as elastic registration output a displacement field comprising a displacement vector for each voxel of one of at least two provided images that are registered, wherein the displacement vector is indicative of a displacement of the voxel necessary for matching the voxel to a corresponding voxel in a respective other one of the at least two provided images. If the provided images refer to 3D images, the displacement vector is preferably a three-dimensional vector indicating the displacement of the respective voxel in three directions. If the provided images refer to 2D images, the displacement vector is preferably a two-dimensional vector indicating the displacement of the respective voxel in two directions. Each voxel of the provided images corresponds to a specific structure or characteristic of the anatomy of the patient in the region of interest. Accordingly, a voxel in one image, for instance, a first image, corresponds to a voxel in another image, for instance, a second image, if the anatomical structure or characteristic of the patient to which the voxel refers is substantially identical. To determine the displacement field, known registration algorithms can be used as, for instance, described in detail in the articles "A survey of medical image registration" by J. B. A. Maintz et al, Medical Image Analysis, volume 2, pages 1 to 36 (1998), and "Deformable Medical Image Registration: A Survey" by A. Sotiras et al., IEEE Transactions on medical imaging, volume 32, pages 1153 to 1190 (2013).

The property determination unit is then adapted to determine the elastic indicator based on the provided displacement field. Preferably, the property determination unit is adapted to determine as elastic indicator for the specific tissue a Jacobian determinant map, an anisotropic deformation index, and/or a strain map. A Jacobian determinant map of the displacement field, an anisotropic deformation index of the displacement field or a strain map of the tissue can be determined, for instance, as described also in the article "Registration-Based Lung Mechanical Analysis of Chronic Obstructive Pulmonary Disease (COPD) Using a Supervised Machine Learning Framework" by S. Bodduluri et al., Academic Radiology, volume 20, pages 527 to 536 (2013). The Jacobian determinant map for a specific tissue region is, for instance, determined by determining a Jacobian determinant for each voxel of the specific tissue region based on the displacement field. Moreover, the property determination unit can further be adapted to determine as elastic indicator an average elastic indicator, which is averaged over elastic indicators of all voxels of the specific tissue region. For instance, the registration unit can be adapted to determine as elastic indicator of a tissue type an average Jacobian determinant from the Jacobian determinant map by averaging the Jacobian determinants determined for each voxel of the specific tissue region.

In an embodiment, the region of interest comprises a lung of a patient comprising a first lung tissue type and a second lung tissue type, wherein the specific tissue determination unit is adapted to determine a first specific tissue region and a second specific tissue region in at least one of the provided images corresponding to the first and the second lung tissue type, and wherein the property determination unit is adapted to determine an elastic indicator for the first and second lung tissue type, respectively. Preferably, in this embodiment, the different states of the region of interest refer to different states of a lung during a breathing cycle. More preferably, the different states include at least one state of the region of interest referring to an end of an inhalation phase and at least one state of the region interest referring to an end of an exhalation phase. Moreover, it is also preferred that the first lung tissue type refers to bronchial tissue and the second lung tissue type refers to parenchyma tissue. Bronchial tissue refers to the bronchioles, being the smallest airways within the airway tree that are not surrounded by any cartilage. Parenchyma tissue consists of alveoli, i.e. air sacs, which provide the gas exchange within the lung. Preferably, the specific tissue determination unit is adapted to determine the bronchial and the parenchyma tissue based on the respective characteristics of the tissue type on the provided image. Bronchioles larger than a voxel size of the provided image can be identified automatically or by a user in the provided image. Bronchioles that are smaller than a voxel size of the provided image cannot be distinguished from parenchymal tissue and are assumed to be part of the parenchymal tissue. In an embodiment, the specific tissue determination unit is further adapted to distinguish between bronchial tissue, parenchyma tissue and bullae, wherein bullae refer to large alveoli that are formed when walls of alveoli are destroyed.

In a preferred embodiment, the provided images comprise at least a first image corresponding to an end of an inhalation phase and at least a second image corresponding to an end of an exhalation phase during a breathing cycle, wherein the registration unit is adapted to register the first and the second image with each other. For instance, the image providing unit can be adapted to provide only the first and the second image. Alternatively, the image providing unit can be adapted to provide, additionally to the first and the second image, images corresponding to intermediate states between the end of the inhalation and the end of the exhalation. The registration unit can in such an embodiment then be adapted, for instance, to register all provided images corresponding to intermediate states to at least one of the first image and the second image.

In an embodiment, the system further comprises a health state determination unit for determining a health state of the patient, wherein the health state determination unit is adapted to determine a phenotype of COPD based on the determined elastic indicator of the parenchyma tissue and the bronchial tissue. It has been found by the inventors that the phenotype of COPD can be determined especially accurately based on the elastic properties of the parenchyma tissue and the bronchial tissue, which are very accurately indicated by the above described system. Preferably, the health state determination unit is adapted to determine as health state that the patient suffers from emphysema as phenotype of COPD, if the elastic indicator for the parenchyma tissue indicates a reduced elasticity of the parenchyma tissue in comparison with healthy parenchyma tissue. Moreover, it is preferred that the health state determination unit is adapted to determine that the patient suffers from obstructive bronchiolitis as phenotype of COPD if the elastic indicator for bronchial tissue indicates an increased stiffness or reduced elasticity in the bronchial tissue in comparison with healthy bronchial tissue. Preferably, a Jacobian determinant map is determined for the parenchyma tissue and the bronchial tissue as elasticity indicator and the health state determination unit is adapted to determine the elasticity of the respective tissue based on the Jacobian map. For instance, the health state determination unit can be adapted to determine from the Jacobian determinant map Jacobian determinants that are increased with respect to the Jacobian determinants of surrounding parenchyma tissue and to determine a reduced elasticity based on the increased Jacobian determinants.

In an embodiment, a system for determining a tissue-specific property in a region of interest of a patient is presented, wherein the region of interest comprises different tissue types, wherein the system comprises a) an image providing unit for providing a first image and a second image of the region of interest, wherein the first image corresponds to a first state of the region of interest and the second image corresponds to a second state of the region of interest, b) a registration unit for elastically registering the first and the second image based on image characteristics of the first and the second image, wherein the registration comprises determining an elastic registration output for registering the first and the second image, c) a specific tissue determination unit for determining a specific tissue region in at least one of the first image and the second image in the region of interest, wherein the specific tissue region comprises all parts of the respective image corresponding to a specific tissue type, d) a specific elastic registration output determination unit for determining for the specific tissue region, a specific elastic registration output based on the elastic registration output, and e) a property determination unit for determining an elastic indicator for the specific tissue region based on the specific elastic registration output, wherein the elastic indicator is indicative of an elastic property of the specific tissue. Preferably, a system for determining a tissue-specific property in a lung of a patient is presented, wherein the lung comprises parenchyma tissue and bronchial tissue, wherein the system comprises a) an image providing unit for providing a first image and a second image of the lung, wherein the first image corresponds to a first state of the lung and the second image corresponds to a second state of the lung, b) a registration unit for elastically registering the first and the second image based on image characteristics of the first and second image, wherein the registration comprises determining an elastic registration output for registering the first and the second image, c) a specific tissue determination unit for determining a first and a second specific tissue region in at least one of the first image and the second image in the lung, wherein the first specific tissue region comprises all parts of the respective image corresponding to parenchyma tissue and the second specific tissue region comprises all parts of the respective image corresponding to bronchial tissue, d) a specific elastic registration output determination unit for determining for the first and the second specific tissue region a first and second specific elastic registration output based on the elastic registration output, and e) a property determination unit for determining a first and a second elastic indicator for the parenchyma tissue and the bronchial tissue based on the first and second specific elastic registration outputs, respectively, wherein the first elastic indicator is indicative of an elastic property of the parenchyma tissue and the second elastic indicator is indicative of an elastic property of the bronchial tissue. Preferably, in this embodiment the system comprises a health state determination unit for determining as health state of the patient if the patient suffers from one phenotype of COPD based on the determined first and second elastic indicator.

In a further aspect of the present invention, a method for determining a tissue-specific property in a region of interest of a patient is presented, wherein the region of interest comprises different tissue types, wherein the method comprises the steps of a) providing at least two images of the region of interest, wherein the provided images correspond to different states of the region interest, b) elastically registering the at least two provided images to each other based on image characteristics of the at least two provided images, wherein the registration results in determining at least one elastic registration output allowing to align the at least two provided images with each other, c) determining a specific tissue region in the region of interest in at least one of the provided images, wherein the specific tissue region comprises all parts of the respective provided image corresponding to a specific tissue type, d) determining for the specific tissue region a specific elastic registration output based on the at least one determined elastic registration output, and e) determining an elastic indicator for the specific tissue type based on the specific elastic registration output of the specific tissue region, wherein the elastic indicator is indicative of an elastic property of the specific tissue type.

In a further aspect of the present invention, a computer program for determining a tissue-specific property in a region of interest of a patient is presented, wherein the computer program comprises program code means for causing the system of claim 1 to carry out the steps of the method as defined in claim 12 when the computer program is executed by a computer controlling the system.

It shall be understood that the system of claim 1, the method of claim 12, and the computer program of claim 13 for determining a tissue-specific property in a region of interest of a patient have similar and/or identical preferred embodiments, in particular as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
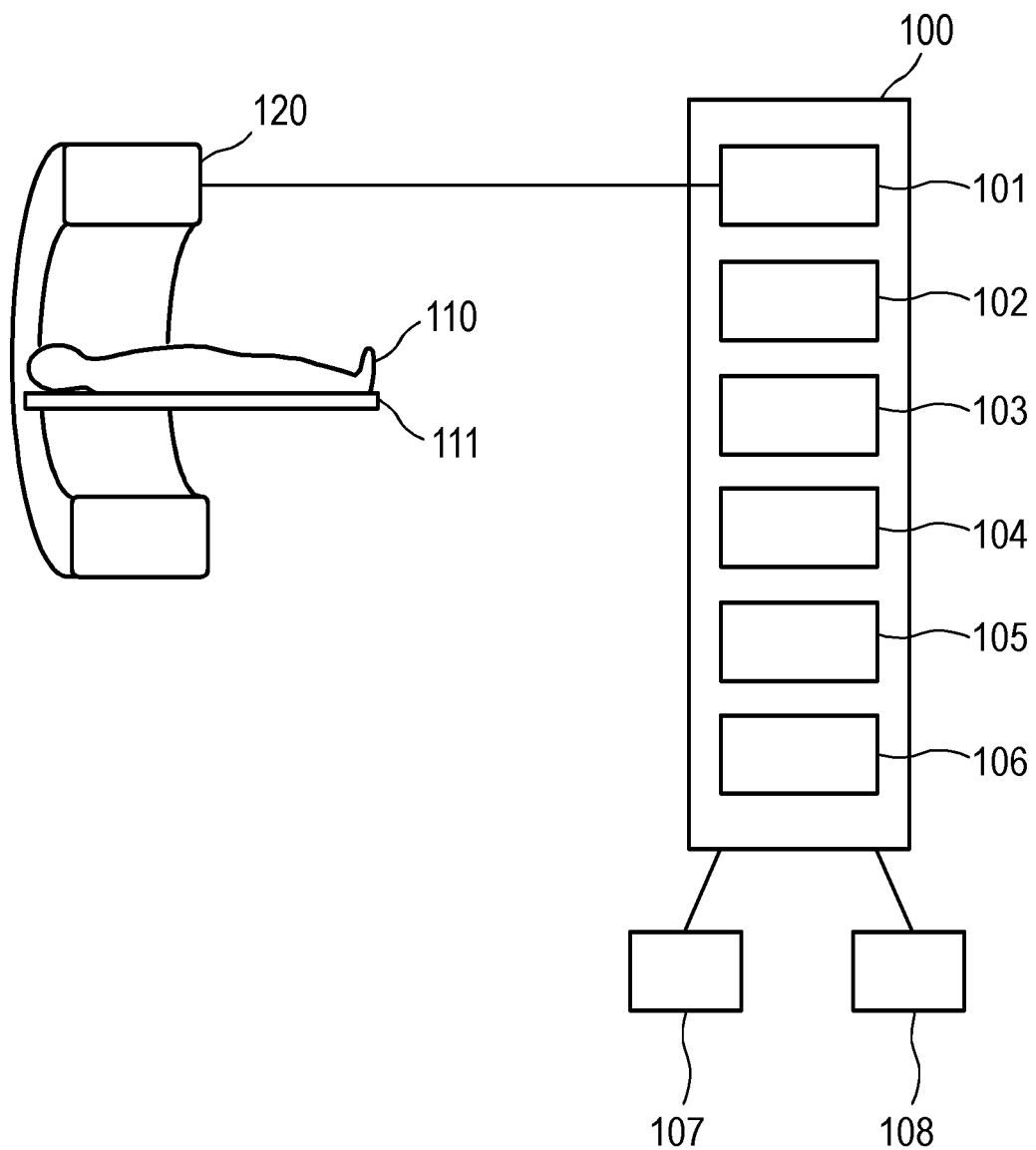
FIG. 1 shows schematically and exemplarily an embodiment of a system for determining a tissue-specific property in a region of interest of a patient.

FIG. 1 shows schematically and exemplarily an embodiment of a system for determining a tissue-specific property in a region of interest of a patient. In this embodiment, the system 100 comprises an image providing unit 101, a registration unit 102, a specific tissue determination unit 103, a specific elastic registration output determination unit 104, a property determination unit 105 and a health state determination unit 106. Further, the system comprises an output unit 107 being, for instance, a display, a printer, a voice output, etc. and an input unit 108, being, for instance, a keyboard, a computer mouse, a touchscreen, etc. In this embodiment, the image providing unit 101 is connected to a medical imaging system used for acquiring a first and a second image of a patient 110 lying on a patient support 111. In this embodiment, the medical imaging system is a CT system 120. In the embodiment described here, the medical imaging system, being a CT system 120, is adapted to acquire a first image of the lung of the patient 110 during an inhalation state of the lung. For instance, the patient 110 can be prompted to inhale as much as possible and to hold his/her breath in this state until the first image has been acquired. Further, the CT system 120 is adapted to acquire a second image of the lung of the patient 110 during an exhalation state. For instance, the patient 110 can be prompted to exhale as much as possible and to hold his/her breath in this state until the second image has been acquired by the CT system 120. The CT system 120 can then provide the first and the second image to the image providing unit 101, wherein the image providing unit 101 can, in this embodiment, be a storage unit for storing the first and the second image. The image providing unit 101 then provides the first and the second image to the registration unit 102.

The registration unit 102 is in this embodiment adapted to automatically register the first and the second image elastically to each other. Since in this embodiment elastic properties of tissue types in a lung are determined, the registration unit 102 can be adapted, for instance, to first segment the lung in the first and the second image. The segmentation can be performed based on known segmentation algorithms. The registration unit 102 can then be adapted to only register the parts of the first and the second image with each other that are segmented as part of the lung. The registration unit 102 can then be adapted to automatically determine image characteristics of the lung in the first and the second image, for instance, structural, i.e. anatomical, characteristics of the lung segmented in the first and the second image, and can then register the first and the second image based on these structural characteristics of the lung. For registering the first and the second image the registration unit 102 is adapted to determine as elastic registration output a displacement field comprising a displacement vector for each voxel being part of the segmented lung in the first image. The displacement value of a voxel is indicative for the displacement of the voxel of the first image necessary to match a corresponding voxel in the second image.

The specific tissue determination unit 103 is in this embodiment then adapted to determine a specific tissue region in at least one of the first image and the second image. In the exemplary embodiment described here, the specific tissue determination unit 103 is adapted to determine a first specific tissue region and a second specific tissue region, wherein the first specific tissue region refers to parenchyma tissue and the second specific tissue region refers to bronchial tissue. The specific tissue determination unit 103 can be adapted, for instance, to differentiate between the first specific tissue and the second specific tissue, for instance, between parenchyma tissue and bronchial tissue, based on the expected gray values and structures of the respective tissue. The specific tissue determination unit 103 then determines all voxels of, for instance, the first image that correspond to parenchyma tissue and determines the first specific tissue region based on the determined voxels. Moreover, the specific tissue determination unit 103 determines all voxels corresponding to bronchial tissue and determines the second specific tissue region based on the determined voxels. Thus, the first and the second specific tissue regions comprise all parts of the first image of the lung corresponding to the respective specific tissue type.

The specific elastic registration output determination unit 104 then determines for each specific tissue region a specific elastic registration output based on the elastic registration parameters. In particular, in this embodiment the specific elastic registration output determination unit 104 determines, for all voxels belonging to the first specific tissue region, the corresponding displacement vectors in the displacement field, wherein these identified displacement vectors then form the specific elastic registration output for the first specific tissue region. Further, in this embodiment the specific elastic registration parameters determination unit 104 is adapted to also determine the specific elastic registration output for the second specific tissue region in accordance with the determination for the first specific tissue region. Thus, a first specific elastic registration output and a second specific elastic registration output is provided by the specific elastic registration output determination unit 104.

The property determination unit 105 is then adapted to determine an elastic indicator for the first specific tissue type and the second specific tissue type individually based on the respective specific elastic registration outputs. In a preferred embodiment, the property determination unit 105 determines a Jacobian determinant for each voxel of the specific tissue region based on the displacement vector of the respective voxel and respective neighboring voxels, wherein the Jacobian determinant is indicative of a local volume change in the region of the voxel due to respiration. The Jacobian determinants determined for each voxel of the specific tissue region then form a Jacobian determinant map of this specific tissue region. The Jacobian determinant map or a derived quantity of the Jacobian determinant map, like an average Jacobian determinant, can be determined as the elastic indicator. Moreover, the property determination unit 105 can also be adapted to determine for one of the specific tissue types an anisotropic deformation index for the specific tissue region as elastic indicator based on the displacement vectors of the specific tissue region, wherein the anisotropic deformation index in this embodiment is indicative of an anisotropy of a deformation of the specific tissue region during respiration. After determining a respective elastic indicator for the parenchyma tissue and the bronchial tissue individually the property determination unit 105 provides the elastic indicator to the health state determination unit 106.

The health state determination unit 106 is in this embodiment adapted to compare the determined elastic indicator, for instance, the Jacobian determinant map or the anisotropic deformation index with respective indicators for parenchyma tissue and bronchial tissue of a healthy human being. Based on this comparison, the property determination unit 105 can be adapted, for instance, to determine a reduced elasticity of the parenchyma tissue indicating that the patient 110 suffers from emphysema as the phenotype of COPD. Moreover, the health state determination unit 106 can be adapted to determine, based on this comparison, that the bronchial tissue shows a higher stiffness than healthy tissue, implying that the patient 110 may suffer from bronchial wall thickening, indicating that the patient 110 suffers from obstructive bronchiolitis as phenotype of COPD. The health state determination unit 106 is then adapted to present the finding with respect to the health state of the patient 110 to a user via the output unit 107.

Figure 2:
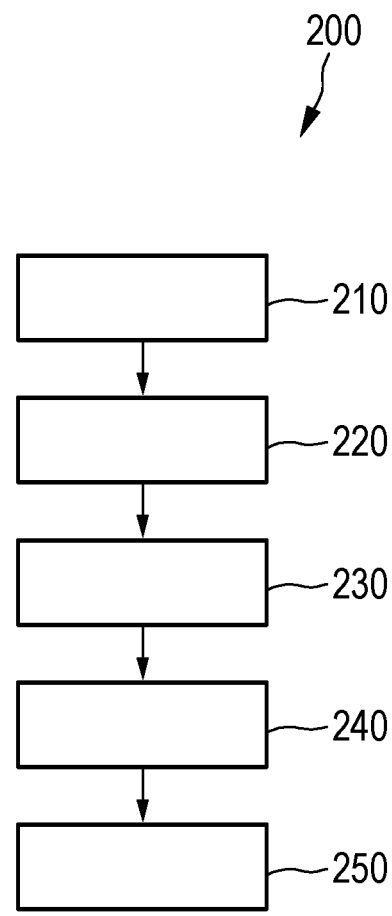
FIG. 2 shows a flowchart exemplarily illustrating an embodiment of a method for determining a tissue-specific property in a region of interest of a patient.

FIG. 2 shows a flowchart exemplarily illustrating an embodiment of a method for determining a tissue-specific property in a region of interest of a patient 110. The method 200 comprises a first step 210 of providing at least two images, for instance, a first image and a second image, of a region of interest. The provided images correspond to different states of the region of interest, for instance, a first image can correspond to a first state of a region of interest and a second image can correspond to a second state of the region of interest. In a preferred embodiment corresponding to the embodiment described above the first state refers to an inhalation state and the second state refers to an exhalation state, wherein the region of interest comprises a lung of the patient 110. Moreover, preferably the first and the second image are acquired using a CT system or an MR system. In a second step 220 the provided images, for instance, the first and the second image, are elastically registered based on image characteristics of the provided images, wherein each provided image is registered to at least one other provided image. The registration comprises determining at least one elastic registration output for the registration of the respective provided images, wherein in a preferred embodiment the elastic registration output corresponds to a displacement field comprising displacement vectors indicating a displacement of each part of an image that is necessary for matching this part of the image to a corresponding part in another image. In a step 230 that can be executed before, during, or after the execution of step 220 a specific tissue region is determined in at least one of the provided images in the region of interest. The specific tissue region comprises all parts of the respective image corresponding to a specific tissue type. In a preferred embodiment a first specific tissue region comprises all voxels of the respective provided image corresponding to parenchyma tissue and a second specific tissue region comprises all voxels of the respective provided image corresponding to bronchial tissue. Further, in step 240 a specific elastic registration output is determined for the specific tissue region based on the at least one elastic registration output. Preferably, for the first specific tissue region and the second specific tissue region a displacement field is determined as specific elastic registration output, wherein the displacement field comprises displacement vectors that correspond to the voxels belonging to the respective region. In a last step 250 an elastic indicator is determined for the specific tissue type based on the specific elastic registration output of the specific tissue region. In a preferred embodiment a Jacobian determinant map and/or an anisotropic deformation index are determined individually for parenchyma tissue and bronchial tissue based on the previously determined displacement field for the first and the second specific tissue region, respectively. It is preferred that further a health state is determined of the patient 110 based on the elastic indicator of the specific tissue type in the region of interest. For example, it is determined that the patient 110 suffers from emphysema if the elastic indicator indicates a reduced elasticity in the parenchyma tissue. As a further example, it can be determined that the patient 110 suffers from obstructive bronchiolitis if the elastic indicator indicates that the bronchial tissue shows a larger stiffness or reduced elasticity with respect to healthy bronchial tissue.

In the above given examples the proposed invention allows to address the need to distinguish between different phenotypes of COPD, referring to emphysema and obstructive bronchiolitis. In one example, it is proposed to perform the estimation of mechanical properties, i.e. elastic properties, independently for lung tissue, i.e. parenchyma tissue, and bronchi, i.e. bronchial tissue. Specifically, for instance, thorax CT images can be acquired during an inhalation and an exhalation state of the patient. In these images a segmentation can be performed to identify the lung. Further, an elastic registration can be performed of the lung in the two images, i.e. the first and the second image. Then, the image voxels of at least one of the two images can be classified in accordance with whether they belong to parenchyma tissue or bronchial tissue. From the registration parameters determined during the registration of the two images, indicators of the elastic properties of the bronchial tissue and the parenchyma tissue can be derived, referring, for instance, to a Jacobian determinant map or a strain map. These elastic indicators can then be analyzed independently for the voxels corresponding to parenchyma tissue and bronchial tissue. It can be assumed that emphysema results in a reduced elasticity of the parenchyma tissue, whereas bronchial wall thickening, i.e. obstructive bronchiolitis, can lead to a larger stiffness of the bronchial tissue.

Although in the above embodiments the region of interest referred to a lung of the patient, the first and the second tissue type referred to parenchyma tissue and bronchial tissue, respectively, and thus the diagnosis referred to determining a specific phenotype of COPD, in other embodiments the region of interest might comprise other organs, for instance, a heart of a patient, comprising different tissue types, such that the diagnosis can refer to different diseases.

Although in the above embodiments the first and the second image were acquired by using a medical CT system, in other embodiments the first and the second image might be acquired by using an MR system, an ultrasound system, a PET system, etc. Moreover, the first and the second image might be acquired by different imaging modalities, for instance, the first image might be acquired with an x-ray imaging system and the second image might be acquired with an ultrasound system.

Although in the above embodiment two images, i.e. a first and a second image, are provided, in other embodiments more than two images can be provided. In these embodiments the registration unit is adapted to register all the provided images with each other, for instance, by registering one of the images with all other images. Moreover, in such embodiments more than one elastic registration output can be determined and more than one specific elastic registration output can be determined based on the more than one elastic registration outputs. Further, in such a case also more than one elastic indicators can be determined based on the more than one specific elastic registration outputs, wherein the health state determination unit can then be adapted to determine the health state of the patient based on the more than one elastic indicators.

Although in the above embodiments the provided images were 3D images of a region of interest, in other embodiments the provided images can also refer to 2D images, for instance, to specific slices through the patient or to respective projection images.

Although in the above embodiments the elastic indicator that was determined referred to a Jacobian determinant map or an anisotropic deformation index, also other indicators for the elastic properties of a tissue could be determined, for instance, a curl of the displacement field or a combination of eigenvalues of an operator being applied to the displacement field can be determined.

Although in the above embodiments the system comprised the health state determination unit, in other embodiments the health state determination unit can be omitted and the system can be adapted to present the elastic indicators of the specific tissue type as result directly to a user, such that the user can determine a health state of a patient him-/herself based on the elastic properties.

Although in the above embodiments the registration unit was adapted to automatically register the first and the second image, in other embodiments the registration unit can be adapted to register the first and the second image in cooperation with the user, for instance, by providing the first and the second image to the user and by prompting the user to indicate structural characteristics of the region of interest in the first and the second image, wherein the registration unit is then adapted to register the first and the second image based on the structural characteristics indicated by the user.

Although in the above embodiments the specific tissue determination unit was adapted to determine the specific tissue region automatically, also the specific tissue determination unit can be adapted to determine the specific tissue region in cooperation with a user. For instance, the specific tissue determination unit can be adapted to display the first and/or the second image to a user and to prompt the user to indicate, for instance, delineate, all regions of the first and/or the second image comprising a specific tissue type, wherein the specific tissue determination unit is then adapted to determine the specific tissue region based on the region indicated by the user.

Other variations to the disclosed embodiments can be understood and effected by those skilled in the art in practicing the claimed invention from the study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the registering of the first and the second image, the determining of a specific tissue region, or the determining of an elastic property performed by one or several units or devices can be performed by any other number of units or devices. The procedures and/or the operations of the system can be implemented as program code means of a computer program and/or as dedicated hardware.

A computer program may be stored/distributed on a suitable medium, such as an optical storage medium or a solid-state storage medium, supplied together with or as part of other hardware, but may also be distributed in other forms, such as via the Internet or other wired or wireless telecommunication systems.

Any reference signs in the claims should not be construed as limiting the scope.

The present invention refers to providing a system that allows to very accurately determine the state of a disease, like COPD, in a patient. The system comprises a unit for providing images of the region of interest corresponding to different states of the region of interest, a unit for elastically registering the images to each other resulting in an elastic registration output, a unit for determining a specific tissue region in an image, a unit for determining a specific elastic registration output for the specific tissue region based on the determined elastic registration output, and a unit for determining an elastic indicator for the specific tissue type based on the specific elastic registration output. Thus, a state of a disease that influences the elastic properties of the specific tissue type can be determined very accurately.

The invention claimed is:

1. A system for determining a tissue-specific property in a region of interest of a patient, comprising:
a memory; and
one or more processors coupled with the memory and configured to:
provide at least two images of the region of interest, wherein the provided images correspond to different states of the region of interest, and wherein the region of interest comprises different tissue types;
elastically register the at least two provided images to each other based on image characteristics of the at least two provided images, wherein the registration results in determining at least one elastic registration output allowing to align the at least two provided images with each other;
determine a specific tissue region that is defined by a specific tissue type and that is in the region of interest in at least one of the provided images, wherein the specific tissue region comprises all parts of the respective provided image that correspond to the specific tissue type;
determine a specific elastic registration output for the specific tissue region based on the at least one determined elastic registration output; and
determine an elastic indicator for the specific tissue type based on the specific elastic registration output of the specific tissue region, wherein the elastic indicator is indicative of an elastic property of the specific tissue type.

2. The system according to claim 1, wherein the one or more processors are further configured to determine a health state of the patient based on the determined elastic indicator of the specific tissue type in the region of interest.

3. The system according to claim 1, wherein the one or more processors are further configured to determine a displacement field comprising a displacement vector for each voxel of one of at least two provided images that are registered as elastic registration output, wherein the displacement vector is indicative of a displacement of the voxel necessary for matching the voxel to a corresponding voxel in a respective other one of the at least two provided images.

4. The system according to claim 3, wherein the one or more processors are further configured to determine as elastic indicator of the specific tissue at least one of a Jacobian determinant map, an anisotropic deformation index, and a strain map.

5. The system according to claim 1, wherein the region of interest comprises a lung of a patient comprising a first lung tissue type and a second lung tissue type, wherein the one or more processors are further configured to determine a first specific tissue region and a second specific tissue region in at least one of the provided images corresponding to the first and the second lung tissue type, and wherein the one or more processors are further configured to determine an elastic indicator for the first and second lung tissue type.

6. The system according to claim 5, wherein the different states of the region of interest refer to different states of the lung during a breathing cycle.

7. The system according to claim 6, wherein the provided images comprise at least a first image corresponding to an end of an inhalation phase and at least a second image corresponding to an end of an exhalation phase during a breathing cycle, wherein the one or more processors are further configured to register the first and the second image with each other.

8. The system according to claim 5, wherein the first lung tissue type refers to bronchial tissue and the second lung tissue type refers to parenchyma tissue.

9. The system according to claim 8, wherein the one or more processors are further configured to:
determine a health state of the patient, and
determine a phenotype of chronic obstrusive pulmonary disease (COPD) based on the determined elastic indicators of the parenchyma tissue and the bronchial tissue.

10. The system according to claim 9, wherein the one or more processors are further configured to determine as health state that the patient suffers from emphysema as phenotype of COPD if the elastic indicator for parenchyma tissue indicates a reduced elasticity of the parenchyma tissue in comparison with healthy parenchyma tissue.

11. The system according to claim 9, wherein the one or more processors are further configured to determine that the patient suffers from obstructive bronchiolitis as phenotype of COPD if the elastic indicator for bronchial tissue indicates an increased stiffness in the bronchial tissue in comparison with healthy bronchial tissue.

12. A method for determining a tissue-specific property in a region of interest of a patient, comprising:
providing at least two images of the region of interest, wherein the provided images correspond to different states of the region interest, and wherein the region of interest comprises different tissue types;
elastically registering the at least two provided images to each other based on image characteristics of the at least two provided images, wherein the registration results in determining at least one elastic registration output allowing to align the at least two provided images with each other;
determining a specific tissue region that is defined by a specific tissue type and that is in the region of interest in at least one of the provided images, wherein the specific tissue region comprises all parts of the respective provided image that correspond to the specific tissue type;
determining a specific elastic registration output for the specific tissue region based on the at least one determined elastic registration output; and
determining an elastic indicator for the specific tissue type based on the specific elastic registration output of the specific tissue region, wherein the elastic indicator is indicative of an elastic property of the specific tissue type.

13. A non-transitory computer-readable medium for storing executable instructions that, when executed by a computer, cause the method of claim 12 to be performed.

* * * * *